(12) United States Patent
Tobin

(10) Patent No.: US 7,517,101 B2
(45) Date of Patent: Apr. 14, 2009

(54) CONVERTIBLE LAMP ARRAY

(76) Inventor: Stephen M. Tobin, 89 Channing Rd., Watertown, MA (US) 02472

( * ) Notice: Subject to any disclaimer, the term of this patent is extended or adjusted under 35 U.S.C. 154(b) by 0 days.

(21) Appl. No.: 11/691,850

(22) Filed: Mar. 27, 2007

(65) Prior Publication Data

US 2007/0283655 A1 Dec. 13, 2007

(51) Int. Cl.
*F21V 7/00* (2006.01)
*H05B 35/00* (2006.01)
(52) U.S. Cl. ............... 362/1; 362/220; 362/239; 362/250; 362/287; 362/427; 607/88; 607/90; 607/91
(58) Field of Classification Search ............ 362/1, 362/2, 11, 184, 197, 200, 234, 220, 250, 362/239, 287, 427, 804; 607/88, 90–94; 606/3, 9, 10; D26/78
See application file for complete search history.

(56) References Cited

U.S. PATENT DOCUMENTS

| 1,847,051 | A | 2/1932 | Zabach |
| 1,859,601 | A | 5/1932 | Rice |
| D260,176 | S | 8/1981 | Boschetti et al. |
| 4,444,189 | A | 4/1984 | Seiverd |
| 4,523,256 | A | 6/1985 | Small |
| 4,680,681 | A | 7/1987 | Fisherman et al. |
| 5,919,217 | A | 7/1999 | Hughes |
| 6,022,119 | A | 2/2000 | Booty, Jr. |
| 6,171,331 | B1 | 1/2001 | Bagraev et al. |
| 6,171,332 | B1 | 1/2001 | Whitehurst |
| 6,176,598 | B1 | 1/2001 | Seligman |
| 6,290,713 | B1 | 9/2001 | Russell |
| 6,419,370 | B1 | 7/2002 | Chen |
| 6,596,016 | B1 | 7/2003 | Vreman et al. |
| 6,602,275 | B1 | 8/2003 | Sullivan |
| 6,645,230 | B2 | 11/2003 | Whitehurst |
| 6,702,837 | B2 | 3/2004 | Gutwein |
| D496,396 | S | 9/2004 | Hyman |
| 6,835,202 | B2 | 12/2004 | Harth et al. |
| D503,426 | S | 3/2005 | Chou |
| 6,896,693 | B2 | 5/2005 | Sullivan |
| D509,014 | S | 8/2005 | Bonneville |
| 2004/0093043 | A1* | 5/2004 | Edel et al. .................. 607/88 |
| 2005/0134524 | A1* | 6/2005 | Parker et al. .............. 345/1.1 |

* cited by examiner

*Primary Examiner*—Stephen F Husar
(74) *Attorney, Agent, or Firm*—Price, Heneveld, Cooper, Dewitt & Litton, LLP

(57) ABSTRACT

A convertible lamp array device comprising a spine member and a first and second side panels rotatably connected to the spine member. The spine member and the first and second side panels have at least one source of light connected thereto. The first side panel and the second side panel can be rotated relative to the spine member into an open position to allow the sources of light emit light towards a target area. The first side panel and the second side panel can be rotated in a second direction relative to the spine member to arrange the device in a closed position for storage of the device. The device is free standing in the open position to allow the device to be used without any external support.

21 Claims, 13 Drawing Sheets

CONVERTIBLE LAMP ARRAY

FIELD OF THE INVENTION

The present invention concerns a lamp for treating human skin disease and cosmetic abnormalities, and more particularly relates to a convertible lamp array.

BACKGROUND OF THE INVENTION

Using light to treat human skin disease and cosmetic abnormalities (e.g., acne) is well known to those skilled in the art. An apparatus is desired to allow the treatment of human skin disease and cosmetic abnormalities in an easier manner.

SUMMARY OF THE PRESENT INVENTION

An aspect of the present invention is to provide a convertible lamp array device comprising a spine member, a first side panel and a second side panel. The spine member has a spine top side and a spine bottom side, with the spine member including at least one spine source of light connected to the spine bottom side of the spine member. The spine member also includes a first side and a second side. The first side panel is rotatably connected to the first side of the spine member. The first side panel includes a first side panel top side and a first side panel bottom side, with the first side panel including at least one first side source of light connected to the first side panel bottom side of the first side panel. The second side panel is rotatably connected to the second side of the spine member. The second side panel includes a second side panel top side and a second side panel bottom side, with the second side panel including at least one second side source of light connected to the second side panel bottom side of the second side panel. The first side panel and the second side panel can be rotated in a first direction relative to the spine member to arrange the device in an open position to allow the at least one spine source of light, the at least one first side source of light and the at least one second side source of light to emit light towards a target area. The first side panel and the second side panel can be rotated in a second direction relative to the spine member to arrange the device in a closed position for storage of the device. The device is free standing in the open position to allow the device to be used without any external support.

Another aspect of the present invention is to provide a convertible lamp array device comprising a spine member, a first side panel, a second side panel, a first wing panel and a second wing panel. The spine member has a spine top side and a spine bottom side, with the spine member including at least one spine source of light connected to the spine bottom side of the spine member. The spine member also includes a first side and a second side. The first side panel is rotatably connected to the first side of the spine member. The first side panel includes a first side panel top side and a first side panel bottom side, with the first side panel including at least one first side source of light connected to the first side panel bottom side of the first side panel. The second side panel is rotatably connected to the second side of the spine member. The second side panel includes a second side panel top side and a second side panel bottom side, with the second side panel including at least one second side source of light connected to the second side panel bottom side of the second side panel. The first wing panel is rotatably connected to the first side panel and the second wing panel is rotatably connected to the second side panel. The device can be placed in an open position with edges of the first wing panel and the second wing panel resting on a support surface and with the spine member, the first side panel and the second side panel being spaced from the support surface.

These and other aspects, objects, and features of the present invention will be understood and appreciated by those skilled in the art upon studying the following specification, claims, and appended drawings.

DETAILED DESCRIPTION OF PREFERRED EMBODIMENTS

Figure 1:
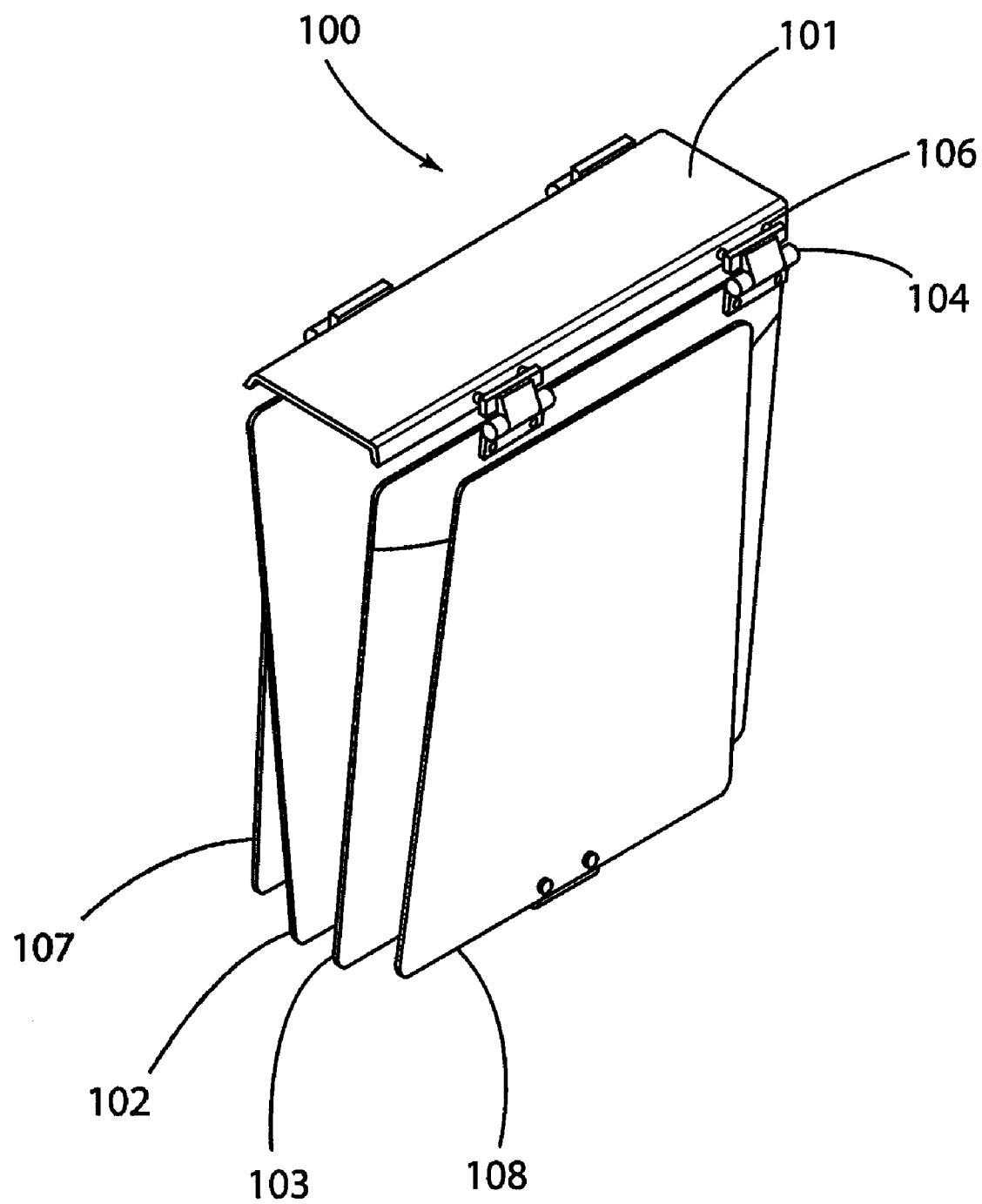
FIG. 1 is a perspective view of a convertible lamp array device of the present invention in a closed position.

For purposes of description herein, the terms "upper," "lower," "right," "left," "rear," "front," "vertical," "horizontal," and derivatives thereof shall relate to the invention as orientated in FIG. 1. However, it is to be understood that the invention may assume various alternative orientations, except where expressly specified to the contrary. It is also to be understood that the specific devices and processes illustrated in the attached drawings, and described in the following specification are simply exemplary embodiments of the inventive concepts defined in the appended claims. Hence, specific dimensions and other physical characteristics relating to the embodiments disclosed herein are not to be considered as limiting, unless the claims expressly state otherwise.

Figure 2:
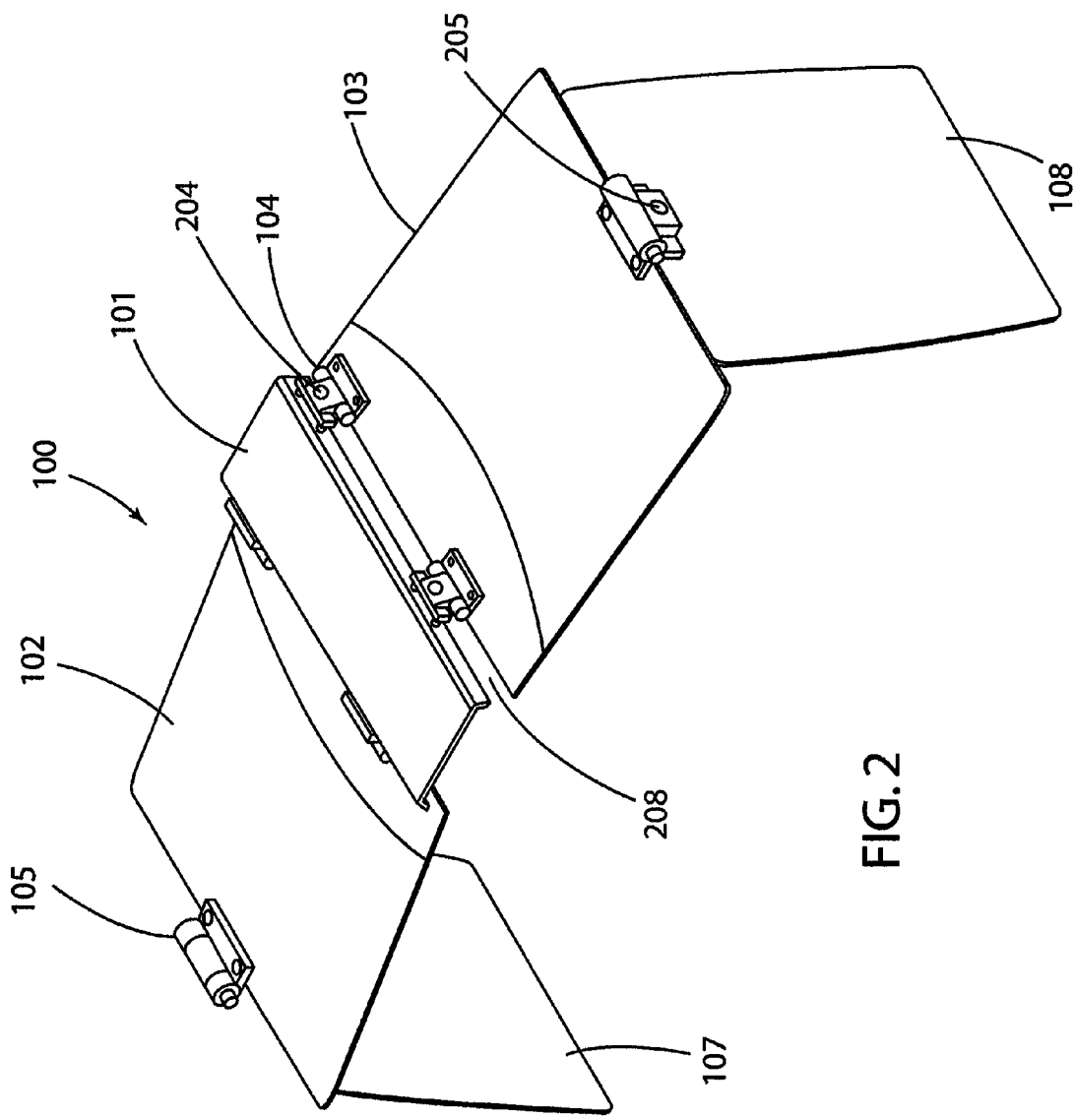
FIG. 2 is a perspective view of the convertible lamp array device of the present invention in a fully open position.
Figure 11:
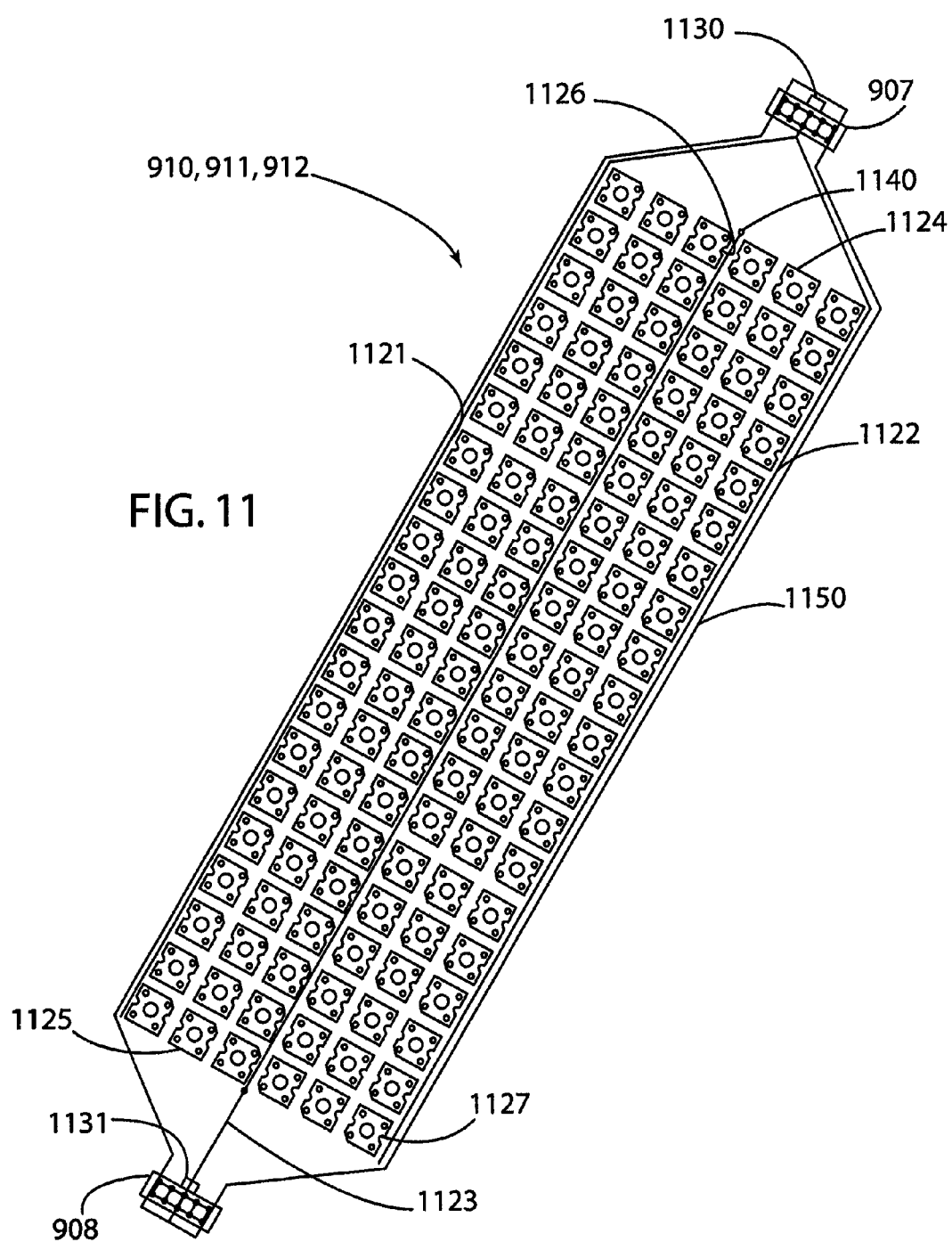
FIG. 11 is a bottom view of a lamp sub-panel of the convertible lamp array device of the present invention.
Figure 12:
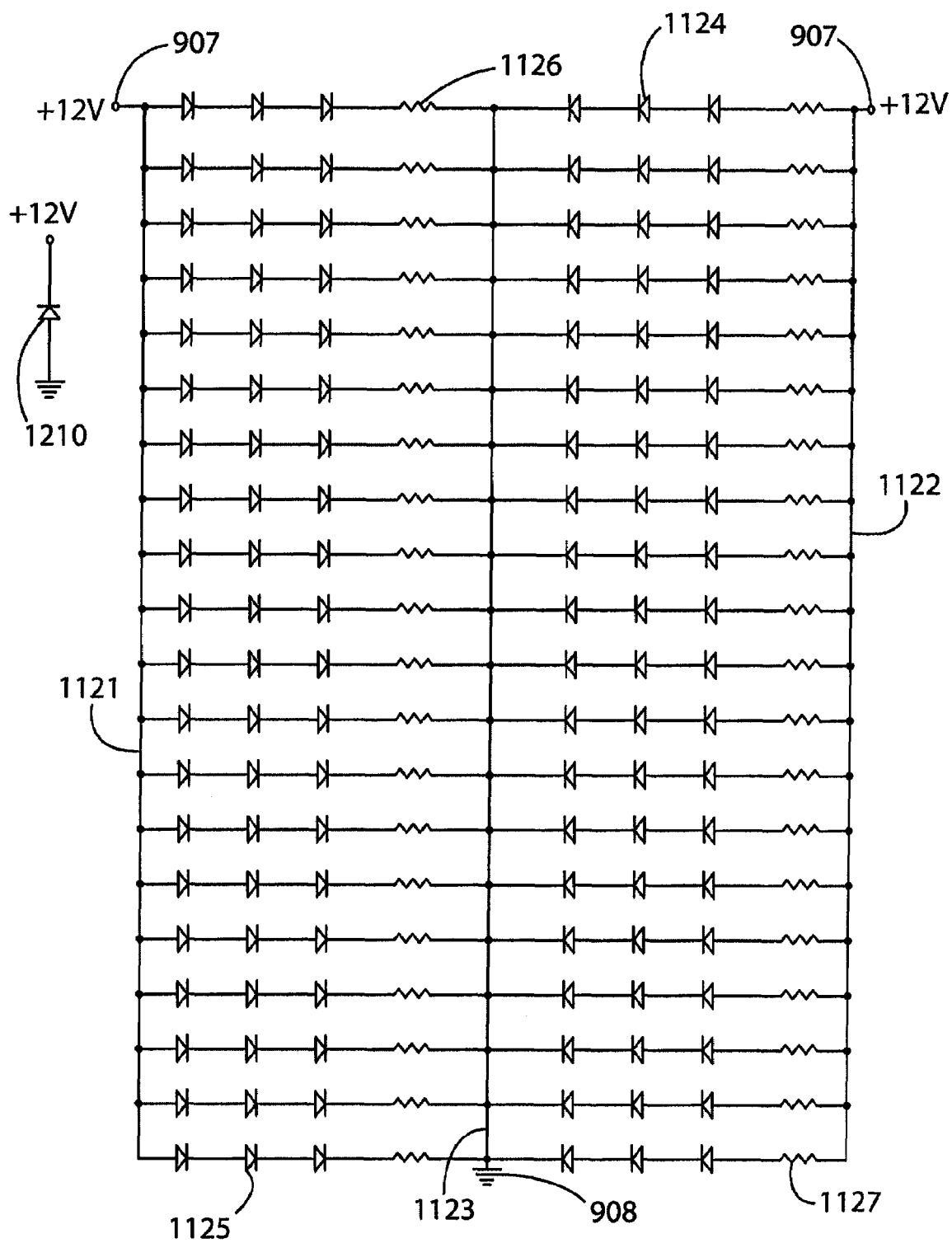
FIG. 12 is a wiring diagram of the lamp sub-panel of the convertible lamp array device of the present invention.

The reference number 100 (FIGS. 1-2) generally designates a convertible lamp array device embodying the present invention. In the illustrated example, the convertible lamp array device 100 comprises a spine 101, a first side panel 102, and a second side panel 103, with the first side panel 102 and the second side panel 103 being rotatably attached to the spine 101. The convertible lamp array device 100 can be used to treat human skin disease and cosmetic abnormalities (e.g., acne) using light alone or in other manners as is well known to those skilled in the art. It is also contemplated that the device 100 could be used for mood improvement, wound healing (as is well known to those skilled in the art), sun tanning, or curing various items (e.g., epoxies). In the illustrated example, the first side panel 102 and the second side panel 103 are rotatably attached to the spine 101 by four upper hinges 104 and eight spacers 106. However, it is contemplated that any number of hinges 104 and spacers 106 could be used or that the first side panel 102 and the second side panel 103 could be rotatably attached to the spine 101 in any manner. Electrical light sources, shown in more detail in FIGS. 11 and 12, are located on inner surfaces of the first side panel 102, the second side panel 103 and a bottom surface of the spine 101. A first wing panel 107 and a second wing panel 108 are rotatably attached to the first side panel 102 and the second side panel 103, respectively. In the illustrated example, the first wing panel 102 and the second wing panel 103 are rotatably attached to the first side panel 102 and the second side panel 103 by lower hinges 105. Although only one hinge 105 is illustrated as connecting the first wing panel 107 and the second wing panel 108 to the first side panel 102 and the second side panel 103, it is contemplated that any number of hinges 105 could be used or that the first wing panel 107 and the second wing panel 108 could be rotatably attached to the first side panel 102 and the second side panel 103 in any manner. It is contemplated that the spine 101, the first side panel 102, the second side panel 103, the first wing panel 107 and the second wing panel 108 could be made of any material that has the strength to support the entire device 100 (e.g., plastic). The hinges 104 and 105 can have a constant torque and/or can be set at a selected rotated position and easily maintained in that position until rotated by a user of the convertible lamp array device 100.

As illustrated in FIG. 1, the convertible lamp array device 100 can be situated in a closed position for moving and storage. Therefore, when the convertible lamp array device 100 is not in use, the convertible lamp array device 100 can be folded up and stored (e.g., on a bookshelf, counter or desk). The convertible lamp array 100 also has a partially open position as illustrated in FIGS. 3A, 3B, 4A, 4B, 7A, 7B, 8A and 8B for treating heads, scalps, arms, legs, hands and feet of a patient as discussed in more detail below. Furthermore, the convertible lamp array 100 includes a fully open position as illustrated in FIGS. 5A, 5B, 6A and 6B for treating chests and backs of male and female patients. The convertible lamp array device 100 can be held in any partially or fully open position by means of a constant holding torque application mechanism contained in hinges 104 and 105. The amount of holding torque applied can be varied by adjustment screws 204 and 205 in the hinges 104 and 105 as is well known to those skilled in the art. Air gaps 208 are created by the spacers 106 between the spine 101 and the first side panel 102 and the second side panel 103, with the air gaps 208 providing ventilation during patient treatment.

Figure 3A:
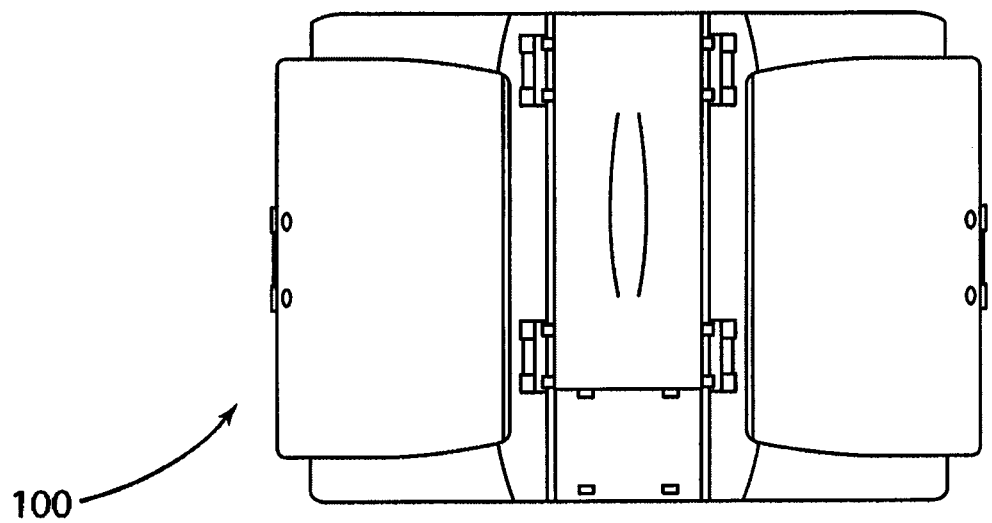
FIG. 3A is a top view of the convertible lamp array device of the present invention treating a face of a patient.
Figure 3B:
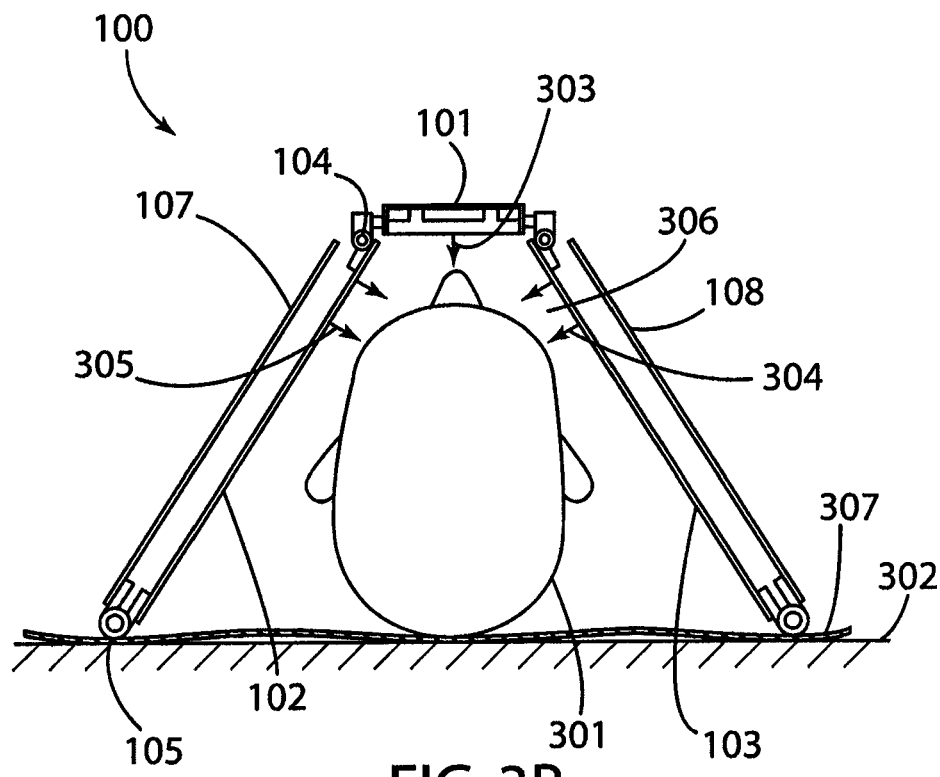
FIG. 3B is a front view of the convertible lamp array device of the present invention treating the face of the patient.

FIGS. 3A and 3B illustrate the convertible lamp array device 100 positioned for treating a face of a patient. During use of the convertible lamp array device 100 for treating the face of the patient, a head 301 of the patient can rest on a disposable exam paper 307, which in turn rests on an exam table 302. Arrows 303-306 show a direction of light propagation from lamp sub-panels 910, 911, 912 connected to the spine 101, the first side panel 102 and the second side panel 103 as shown in more detail in FIGS. 9-12. In this arrangement, five lamp sub-panels are attached to the convertible lamp array device 100, although other arrangements are possible. Light propagates along a first arrow 303 from at least one lamp sub-panel 910 (see FIG. 9) attached to the spine 101. Light also propagates along a second arrow 305 from one or more lamp sub-panels 911 (see FIG. 9) attached to the first side panel 102. Light further propagates along line 304 from one or more lamp sub-panels 912 (see FIG. 9) attached to the second side panel 103. An air space 306 is maintained between a surface of the head 301 of the patient and a surface of the lamps. In this configuration and all configurations below, the size of the air space 306 is adjustable via the hinges 104.

Figure 4:
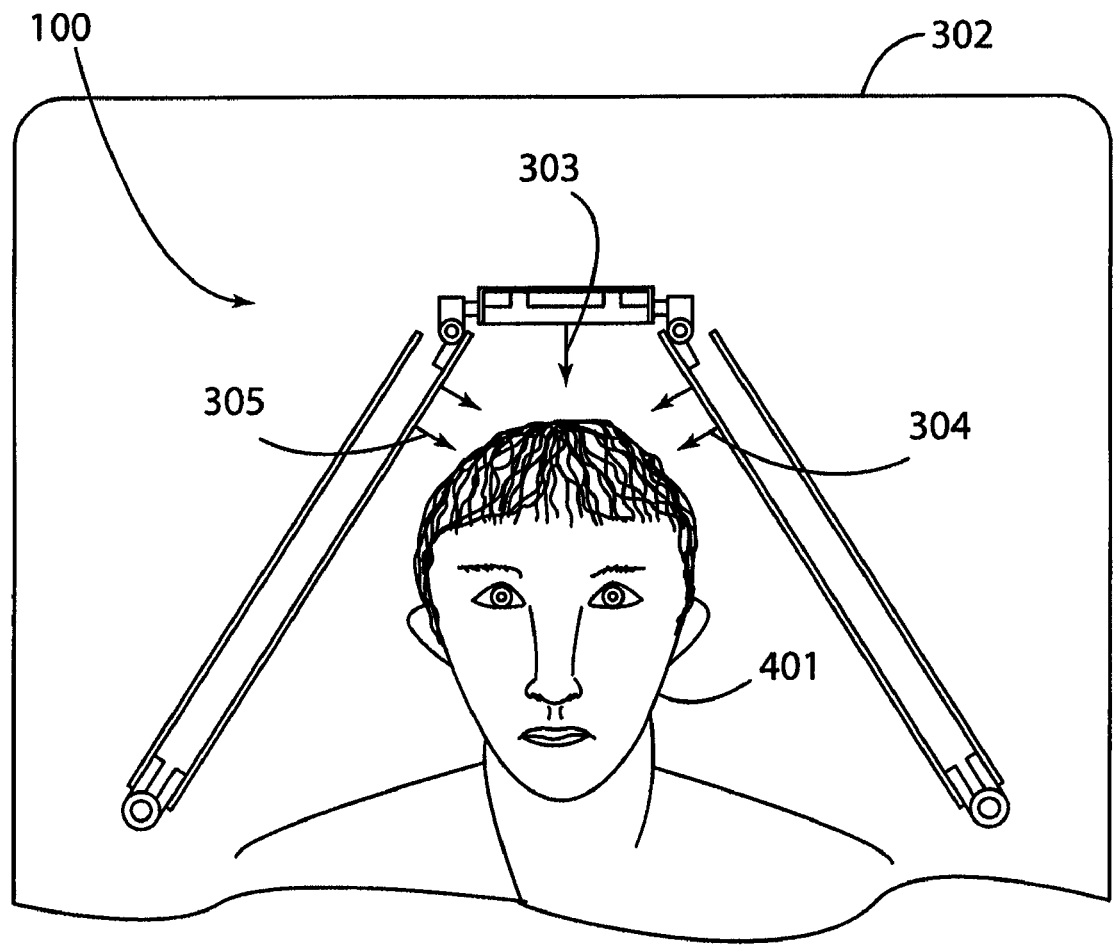
FIG. 4 is a top view of the convertible lamp array device of the present invention treating a scalp of a patient.

FIG. 4 illustrates the convertible lamp array device 100 positioned for treating a scalp of a patient 401. In this arrangement, light propagates along a first arrow 303 from at least one lamp sub-panel 910 attached to the spine 101. Light also propagates along a second arrow 305 from one or more lamp sub-panels 911 attached to the first side panel 102. Light further propagates along line 304 from one or more lamp sub-panels 912 attached to the second side panel 103. The air space 306 is maintained between the scalp of the patient and a surface of the lamps.

Figure 5A:
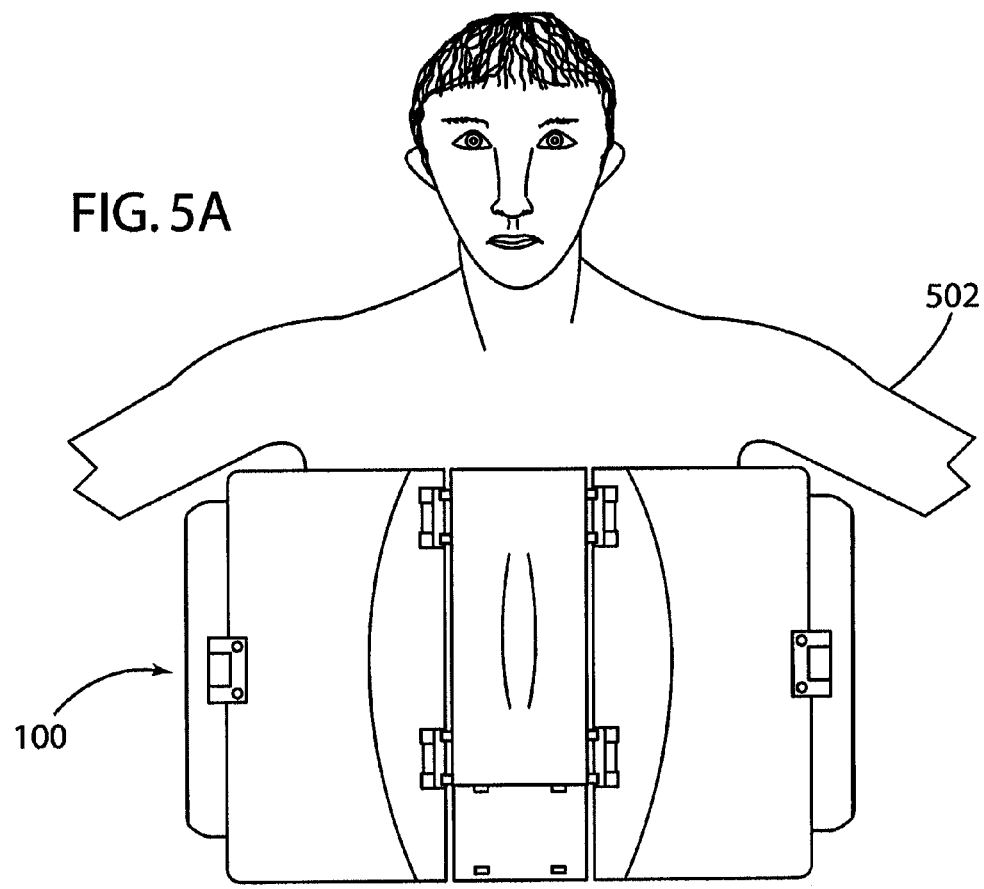
FIG. 5A is a top view of the convertible lamp array device of the present invention treating a back or chest of a patient.
Figure 5B:
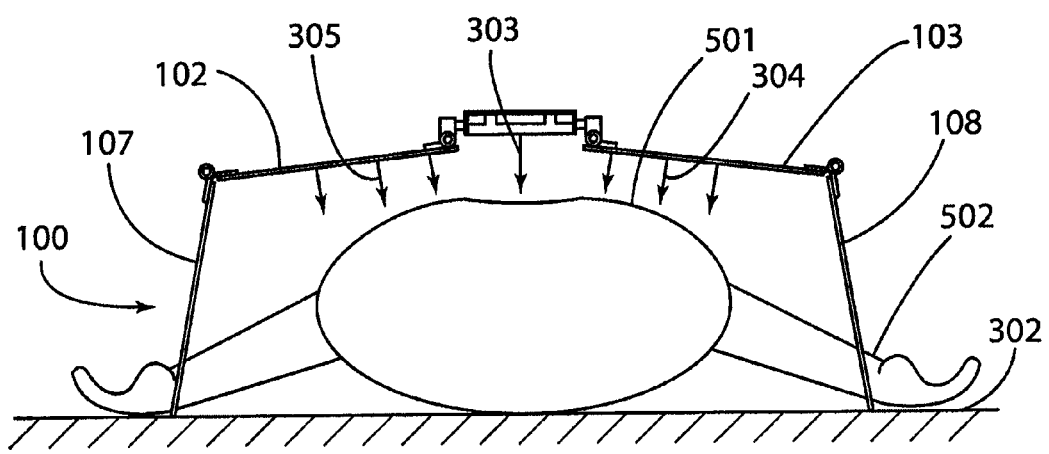
FIG. 5B is a front view of the convertible lamp array device of the present invention treating the back or chest of the patient.

FIGS. 5A and 5B illustrate the convertible lamp array device 100 positioned for treating a chest or back 501 of a patient. In this configuration, arms 502 of the patient are not involved in treatment and are shown passing to the outside of the first wing panel 107 and the second wing panel 108. In this arrangement, light propagates along a first arrow 303 from at least one lamp sub-panel 910 attached to the spine 101. Light also propagates along a second arrow 305 from one or more lamp sub-panels 911 attached to the first side panel 102. Light further propagates along line 304 from one or more lamp sub-panels 912 attached to the second side panel 103. The air space 306 is maintained between the chest or back 501 of the patient and a surface of the lamps.

Figure 6A:
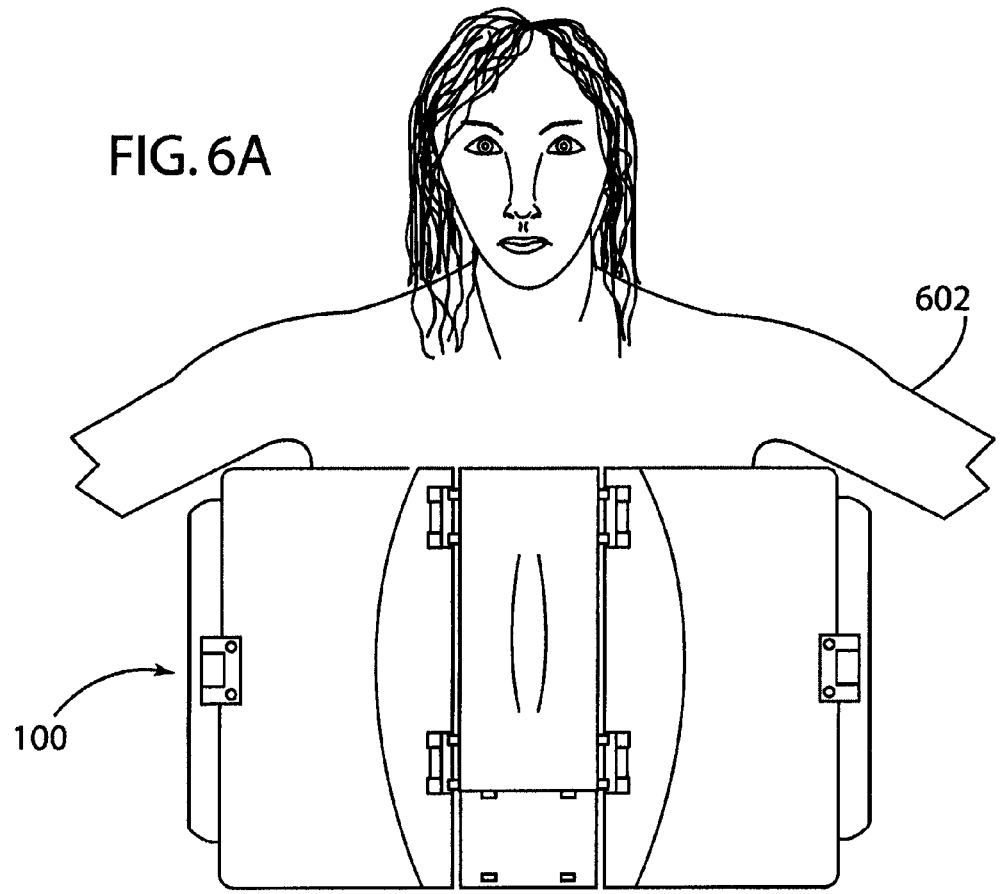
FIG. 6A is a top view of the convertible lamp array device of the present invention treating a chest of a female patient.
Figure 6B:
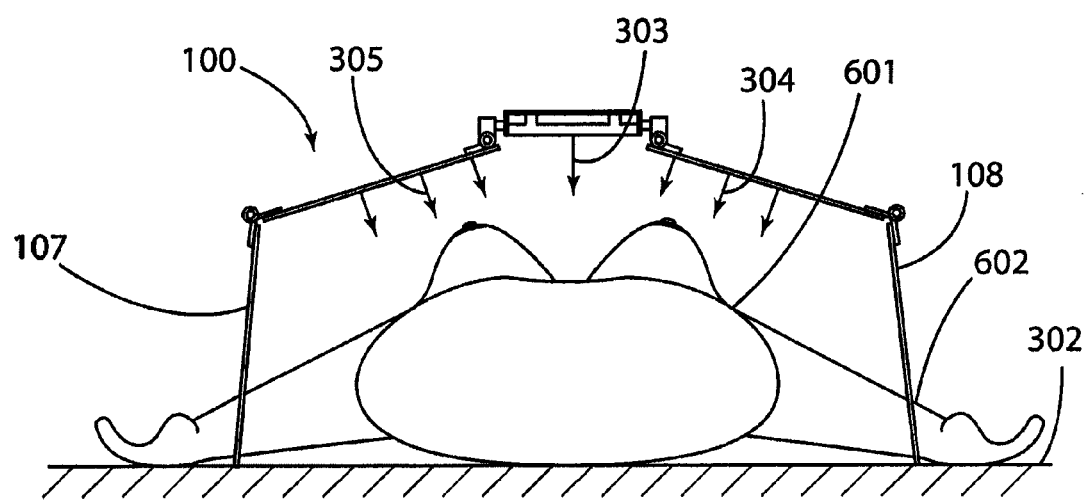
FIG. 6B is a front view of the convertible lamp array device of the present invention treating the chest of the female patient.

FIGS. 6A and 6B illustrate the convertible lamp array device 100 positioned for treating a chest 601 of a female patient. In this configuration, arms 502 of the patient are not involved in treatment and are shown passing to the outside of the first wing panel 107 and the second wing panel 108. In this arrangement, light propagates along a first arrow 303 from at least one lamp sub-panel 910 attached to the spine 101. Light also propagates along a second arrow 305 from one or more lamp sub-panels 911 attached to the first side panel 102. Light further propagates along line 304 from one or more lamp sub-panels 912 attached to the second side panel 103. The air space 306 is maintained between the chest 601 of the patient and a surface of the lamps.

Figure 7A:
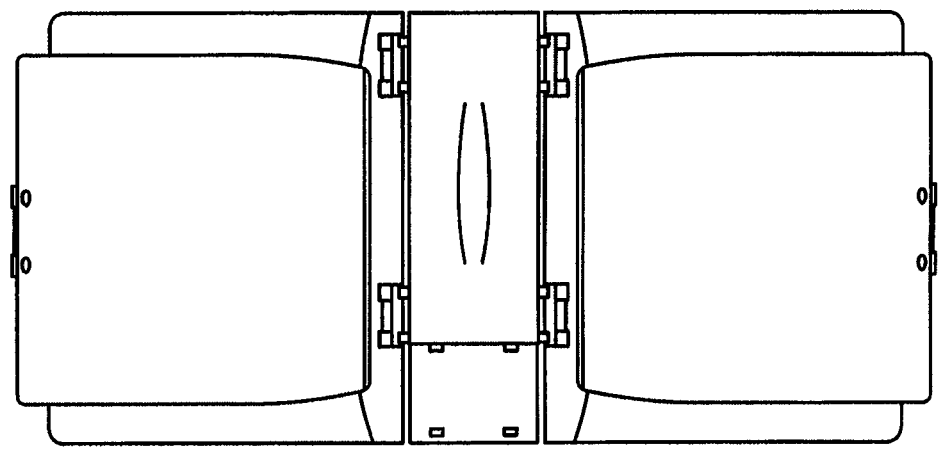
FIG. 7A is a top view of the convertible lamp array device of the present invention treating an arm or leg of a patient.
Figure 7B:
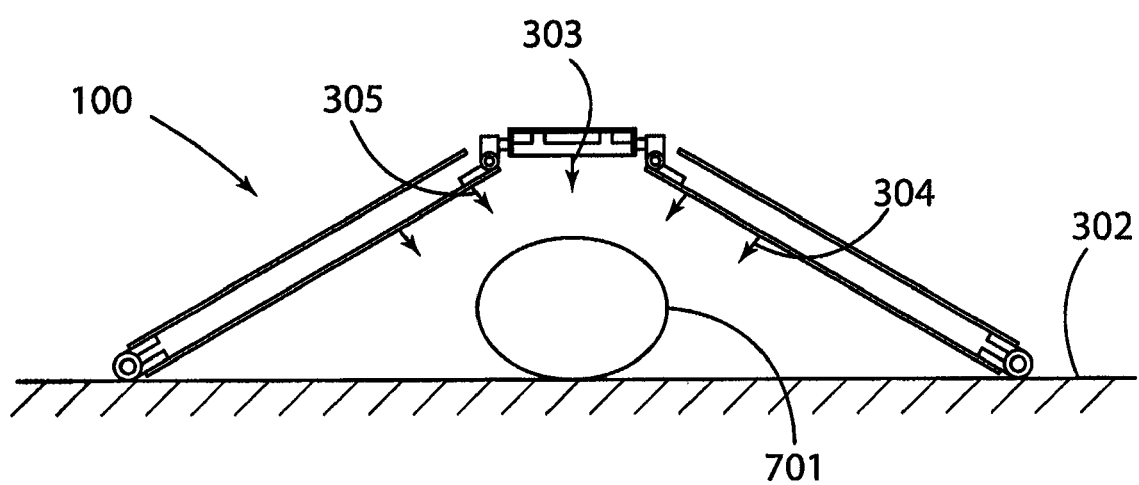
FIG. 7B is a front view of the convertible lamp array device of the present invention treating the arm or leg of the patient.

FIGS. 7A and 7B illustrate the convertible lamp array device 100 positioned for treating an arm or leg 701 of a patient. In this arrangement, light propagates along a first arrow 303 from at least one lamp sub-panel 910 attached to the spine 101. Light also propagates along a second arrow 305 from one or more lamp sub-panels 911 attached to the first side panel 102. Light further propagates along line 304 from one or more lamp sub-panels 912 attached to the second side panel 103. An air space 306 is maintained between the arm or leg 701 of the patient and a surface of the lamps.

Figure 8A:
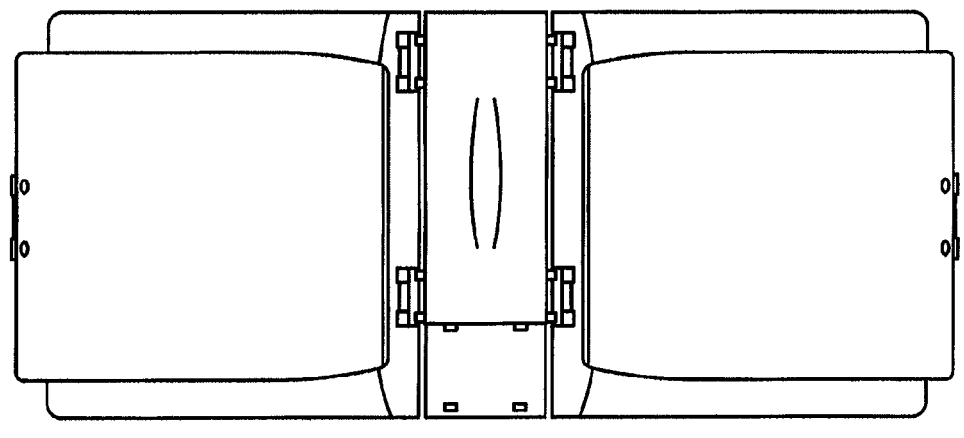
FIG. 8A is a top view of the convertible lamp array device of the present invention treating hands or feet of a patient.
Figure 8B:
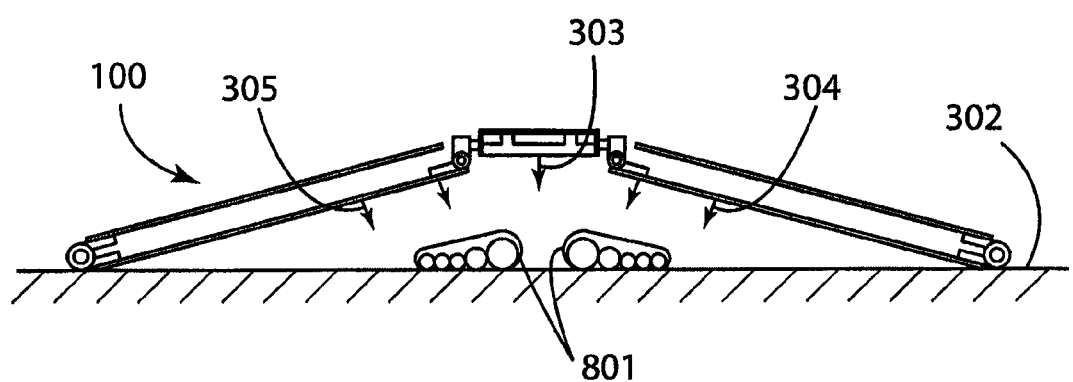
FIG. 8B is a front view of the convertible lamp array device of the present invention treating the hands or feet of the patient.

FIGS. 8A and 8B illustrate the convertible lamp array device 100 positioned for treating hands or feet 801 of a patient. In this arrangement, light propagates along a first arrow 303 from at least one lamp sub-panel 910 attached to the spine 101. Light also propagates along a second arrow 305 from one or more lamp sub-panels 911 attached to the first side panel 102. Light further propagates along line 304 from one or more lamp sub-panels 912 attached to the second side panel 103. The air space 306 is maintained between the hands or feet 801 of the patient and a surface of the lamps.

Figure 9:
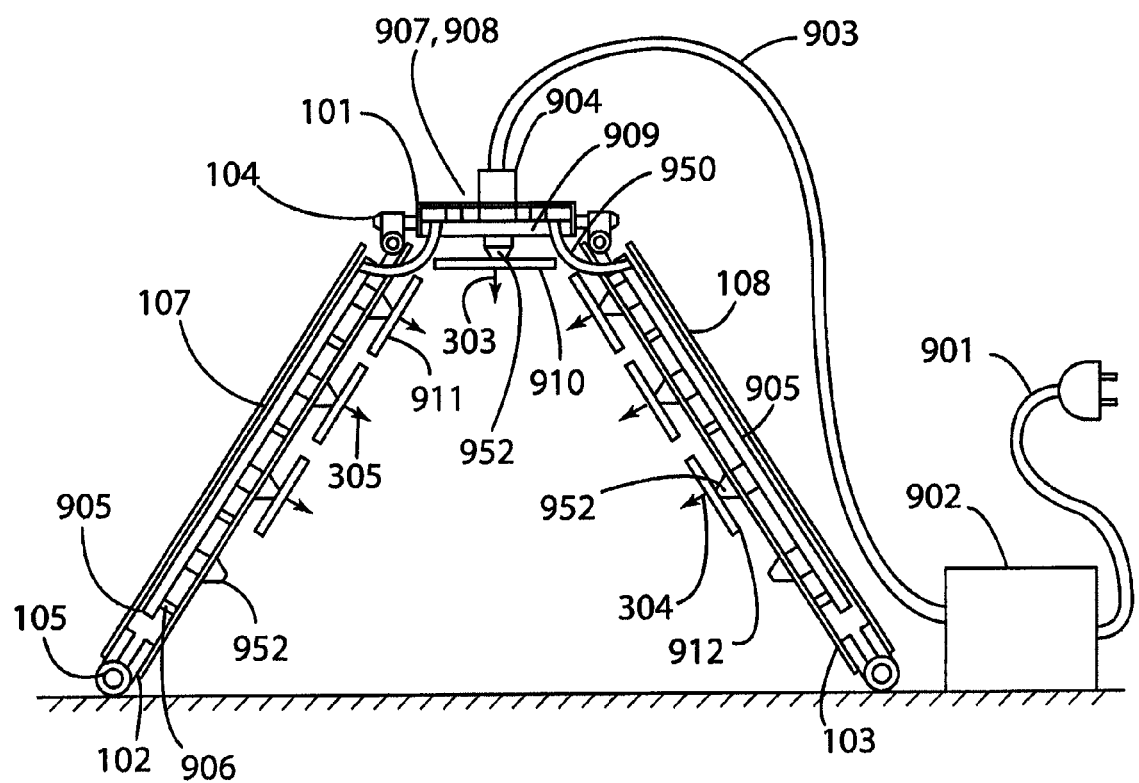
FIG. 9 is a front view of the convertible lamp array device of the present invention illustrating lamp mounting details and power supply connections.

FIG. 9 illustrates lamp mounting details and power supply connections of the convertible lamp array device 100. In the illustrated example, an AC input power cord 901 supplies alternating current to an isolated AC-to-DC adapter 902. Direct current at a voltage preferably at or below 48V is supplied through a direct current cable 903 to the spine 101. It is contemplated that the direct current cable 903 may be connected or disconnected to the spine 101 with a detachable connector 904. The detachable connector 904 is attached to the spine 101 to provide power distribution to a printed circuit board 909 on the spine 101. Other means of powering the device 100 are contemplated (e.g., batteries).

Figure 10:
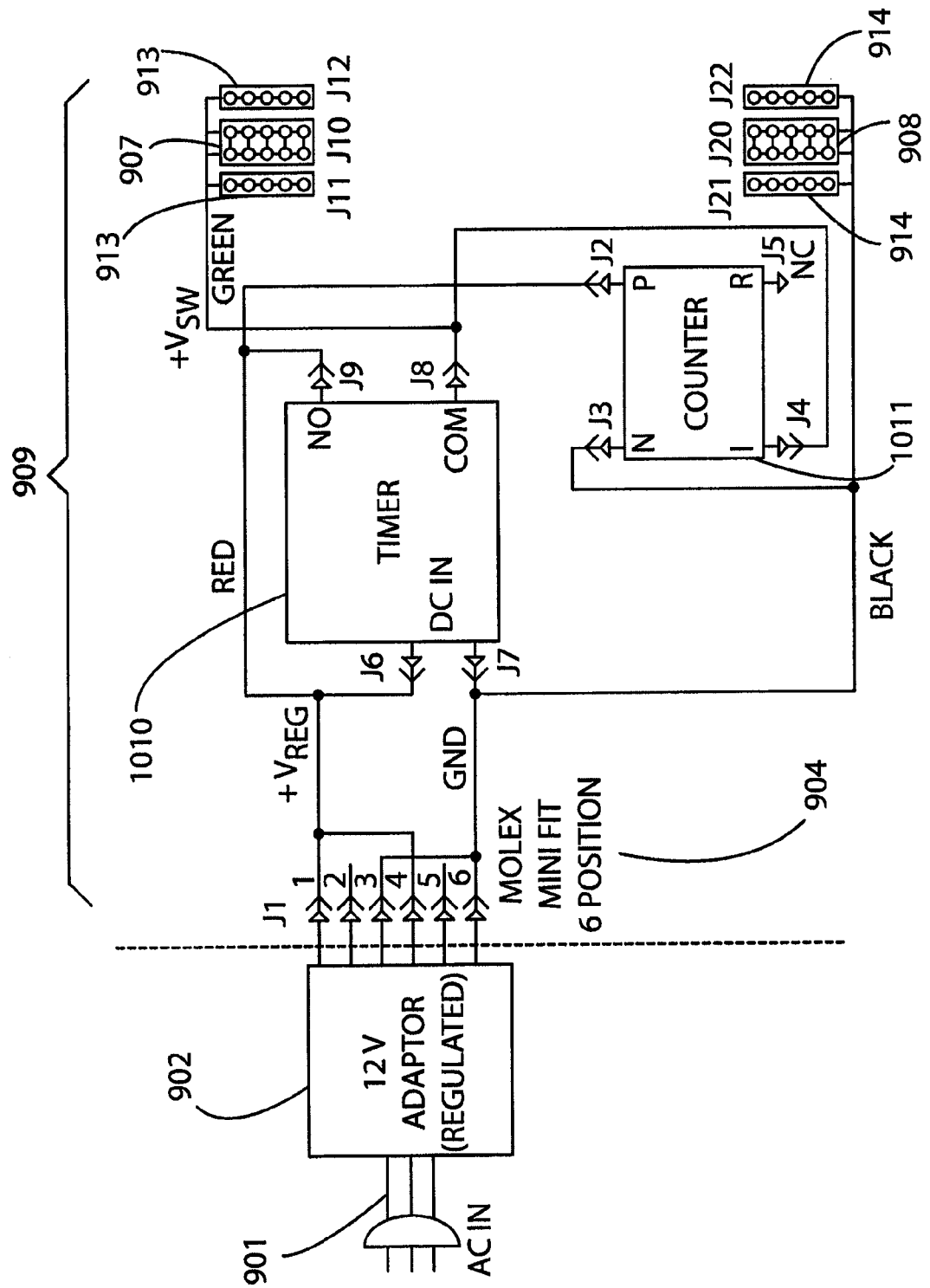
FIG. 10 is a wiring diagram of the convertible lamp array device of the present invention.

In the illustrated example, electrical connections are made from the printed circuit board 909 to lamp sub-panels 911 and 912 by first providing an electrical connection from the printed circuit board 909 to first and second side panel power distribution printed circuit boards 905 on the first side panel 102 and the second side panel 103 via flexible cables 950 having positive polarity 913 and negative polarity 914 (see FIG. 10). The electrical connections are then made to the lamp sub-panels 911 and 912 by lamp sub-panel detachable connectors 952 having positive polarity 907 and negative polarity 908 (see FIG. 10). Electrical connections are made to the lamp sub-panel 910 via a detachable connector 952 interacting with the printed circuit board 909. The lamp sub-panels 910, 911 and 912 are preferably detachably coupled to the lamp sub-panel detachable connectors 952. Spacers 906 in part determine positions of the lamp sub-panels 910, 911 and 912 with respect to the patient being treated. It is contemplated that some of the connectors 952 may have lamp sub-panels 910, 911 and 912 not attached to them, depending on the parts of the body most likely to be treated.

FIG. 10 illustrates a wiring diagram for the convertible lamp array device 100, including the power input and spine power distribution. The side panel power distribution to the first side panel 102 and the second side panel 103 is repetitive and is shown in more detail in FIG. 12. As illustrated in FIG. 10, a digital timer 1010 with a relay output can be provided. It is contemplated that the digital timer 1010 can be mounted to the spine 101 (or other parts of the device) to display and control duration of light exposure to the patient. A counter 1011 can also be provided to record and display the number of hours that the lamp sub-panels have been powered. It is contemplated that the counter 1011 can also be mounted to the spine 101 or other parts of the device 100.

FIG. 11 illustrates a bottom view of the lamp sub-panels 910, 911 or 912. A plurality of light emitting diodes 1124 and 1125 are shown mounted on a printed circuit board 1150. The plurality of light emitting diodes 1124 and 1125 provide the light for treating the human skin disease and cosmetic abnormalities. However, it is contemplated that any light source that can treat human skin disease and cosmetic abnormalities could be used. A positive polarity trace 1121 runs along the left side of printed circuit board 1150, and a positive polarity trace 1122 runs along the right side of printed circuit board 1150. A negative polarity trace 1123 runs along the longer aspect centerline of the printed circuit board 1150. On the left half of the board, a ballast resistor 1126 resides near the center of the board. On the right half of said board, a ballast resistor 1127 resides near the right edge of said board. The positive polarity 907 portion of the connector 952 is provided with a polarization tab 1130 pointed upward and the negative polarity 908 of the connector 952 is provided with a similar polarization tab 1131 pointed upward. A plurality of drilled through holes 1140 are provided for ventilation as required.

FIG. 12 illustrates a wiring diagram of one of the lamp sub-panels 910, 911 or 912. A plurality of light emitting diodes 1124 and 1125 are shown connected in a series and parallel fashion. The values of the ballast resistors 1126 and 1127 can be chosen to determine the current in any series chain of three light emitting diodes 1124 or 1125. A reverse polarity protection diode 1210 may also be provided on the printed circuit board.

Figure 2A:
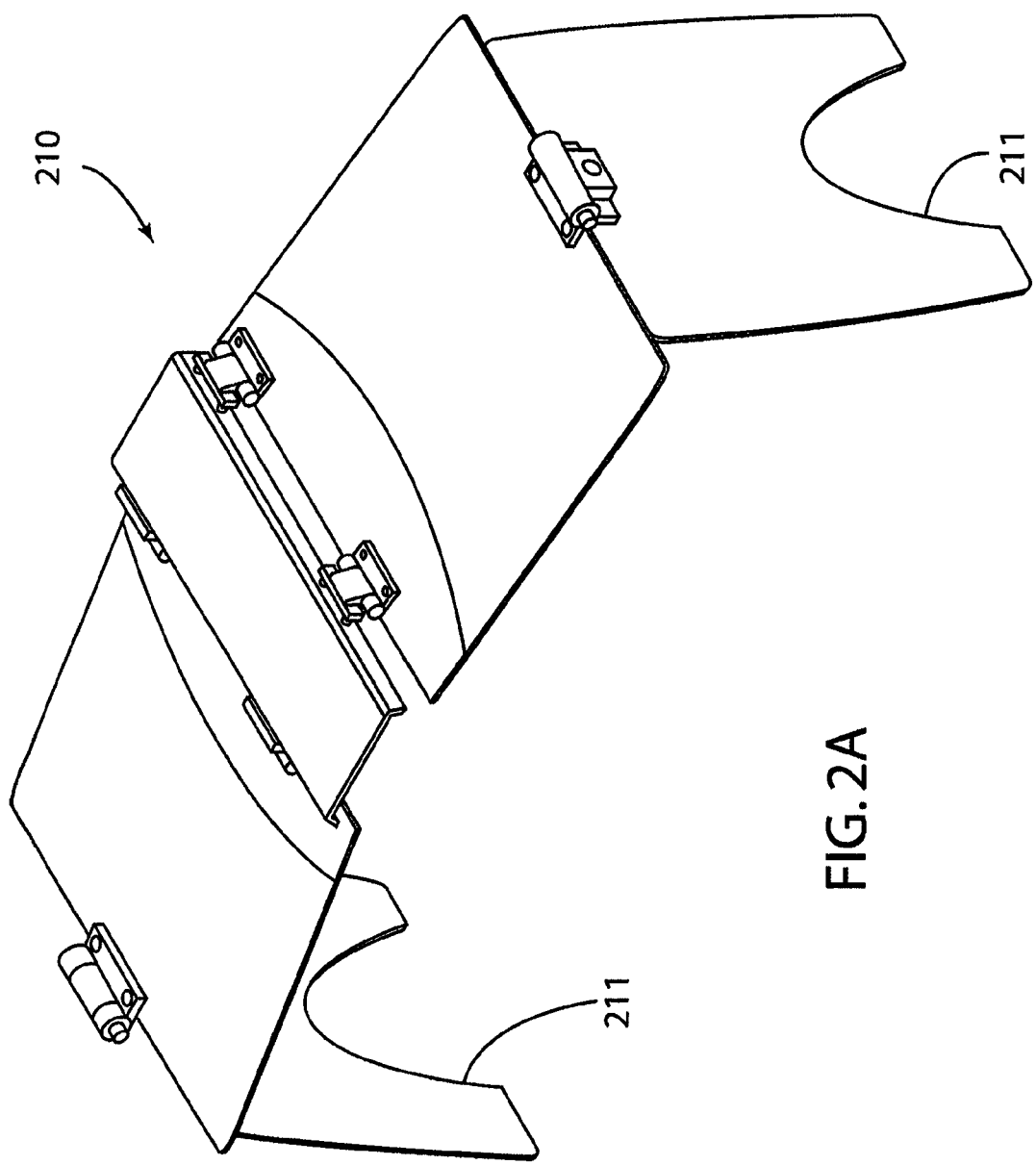
FIG. 2A is a perspective view of a second embodiment of the convertible lamp array device of the present invention in an open position.

The reference numeral 210 (FIG. 2A) generally designates another embodiment of the present invention, having a second embodiment for the convertible lamp array device. The convertible lamp array device 210 is similar to the previously described convertible lamp array device 100, with the addition of a rounded slot 211 in the first wing panel 107 and the second wing panel 108. With the second embodiment of the convertible lamp array device 210, the arms 502 of a patient can pass through the rounded slots 211 in the first wing panel 107 and the second wing panel 108 when the chest or back of the patient are being treated as illustrated above in FIGS. 5A and 5B. The second embodiment of the convertible lamp array device 210 can also be used to treat the face, scalp, arm, legs, feet and hands of a patient as discussed above in regard to the first embodiment of the convertible lamp array device 100.

Various alterations to the methods of treatment using the convertible lamp array device 100 and the construction of the convertible lamp array device 100 are contemplated. For example, it is contemplated that: (1) thumb screws or Phillips headed screws can be used in the hinges 104 and 105 to adjust the position of the hinges 104 and 105; (2) the arm, leg, hand or foot of a patient can be raised above the exam table with a folded towel, pillow or pad; (3) the wing panels 107 and 108 can include fasteners when not in use for connection to the side panels 102 and 103; (4) one or more fans can be used to enhance patient comfort (e.g., mounted in the spine 101); (5) the number of lamp sub-panels can vary depending on the size and location of the area being treated; (6) each pair of top hinges could be formed into a single hinge; (7) each bottom hinge could be divided into two or more separate hinges; (8) a clip could be added to one or both wing panels for holding a patient chart; (9) an integrated circuit could be added to the lamp sub-panels to control the current in each series chain of lamps; (10) one or more light detectors can be added to the bottom side of each lamp sub-panel to control the dose of light given to the patient; (11) a detachable detector can be added on a cable to the spine to enable a self-calibration of light intensity at a given point or points in the treatment zone; (12) in treatments where wing panels are otherwise unused, the wing panels could be folded downward to contact the exam table in order to provide an independent height adjustment; and (13) the circuit board 909 could include LEDs for emitting light towards the patient. Other modifications are also contemplated.

Aspects of the convertible lamp array devices 100 and 210 of the present invention include an absence of heat sinks and stands to produce a smaller, lighter device that can be carried by a clinician from room to room, a constant-torque application mechanism that resides in the hinges to produce a device that is self-supporting, illumination panels that comprise one smaller, rectangular panel bounded on both longer sides by two larger, substantially square panels to product a device that emits a more uniform distribution of radiation onto a face and nose of a patient and that can be collapsed by folding for storage in a relatively small spatial volume, two hinged, non-illuminated panels for producing a device that can be converted by a clinician to treat differently sized areas of the human body (e.g., face and back) by a simple folding and unfolding manipulation of the device, a low-voltage operation and open construction that results in a device that is electrically safe and well ventilated, and lamp sub-panels of similar size with connection/disconnection points that produces a device that can be repaired by a person not skilled in the art.

It is to be understood that variations and modifications can be made on the aforementioned structure without departing from the concepts of the present invention, and further it is to be understood that such concepts are intended to be covered by the following claims unless these claims by their language expressly state otherwise.

I claim:

1. A convertible lamp array device comprising:
   a spine member having a spine top side and a spine bottom side, the spine member including at least one spine source of light connected to the spine bottom side of the spine member, the spine member also including a first side and a second side;
   a first side panel rotatably connected to the first side of the spine member, the first side panel including a first side panel top side and a first side panel bottom side, the first side panel including at least one first side source of light connected to the first side panel bottom side of the first side panel;
   a second side panel rotatably connected to the second side of the spine member, the second side panel including a second side panel top side and a second side panel bottom side, the second side panel including at least one second side source of light connected to the second side panel bottom side of the second side panel;
   wherein the first side panel and the second side panel can be rotated in a first direction relative to the spine member to arrange the device in an open position to allow the at least one spine source of light, the at least one first side source of light and the at least one second side source of light to emit light towards a target area;
   wherein the first side panel and the second side panel can be rotated in a second direction relative to the spine member to arrange the device in a closed position for storage of the device; and
   wherein the device is free standing in the open position to allow the device to be used without any external support;
   a first wing panel rotatably connected to the first side panel; and
   a second wing panel rotatably connected to the second side panel;
   wherein the device can be placed in an open position with edges of the first wing panel and the second wing panel resting on a support surface and with the spine member, the first side panel and the second side panel being spaced from the support surface; and
   wherein the first wing panel and the second wing panel do not include any sources of light.

2. The convertible lamp array device of claim 1, wherein: the first wing panel is connected to the first side panel by at least one first wing constant torque hinge; and the second wing panel is connected to the second side panel by at least one second wing constant torque hinge.

3. The convertible lamp array device of claim 1, wherein: the first side panel is connected to the spine member by at least one first side constant torque hinge; and the second side panel is connected to the spine member by at least one second side constant torque hinge.

4. The convertible lamp array device of claim 1, wherein: at least one spine source of light, the at least one first side source of light and the at least one second side source of light each comprise light emitting diodes.

5. The convertible lamp array device of claim 1, wherein: when the device is in the closed position, a first angle between the spine bottom side of the spine member and the first side panel bottom side is acute, and a second angle between the spine bottom side of the spine member and the second side panel bottom side is acute.

6. The convertible lamp array device of claim 1, further including:
   a digital timer connected to the spine member, the first side panel or the second side panel to display and control a duration of light exposure.

7. The convertible lamp array device of claim 1, further including: a counter connected to the spine member, the first side panel or the second side panel to record and display a number of hours that the sources of light have been powered.

8. A lamp array device comprising:
   a spine member having a spine top side and a spine bottom side, the spine member including at least one spine source of light connected to the spine bottom side of the spine member, the spine member also including a first side and a second side;
   a first side panel rotatably connected to the first side of the spine member, the first side panel including a first side panel top side and a first side panel bottom side, the first side panel including at least one first side source of light connected to the first side panel bottom side of the first side panel;
   a second side panel rotatably connected to the second side of the spine member, the second side panel including a second side panel top side and a second side panel bottom side, the second side panel including at least one second side source of light connected to the second side panel bottom side of the second side panel;
   wherein the first side panel and the second side panel can be rotated in a first direction relative to the spine member to arrange the device in an open position to allow the at least one spine source of light, the at least one first side source of light and the at least one second side source of light to emit light towards a target area;
   wherein the first side panel and the second side panel can be rotated in a second direction relative to the spine member to arrange the device in a closed position for storage of the device; and
   wherein the device is free standing in the open position to allow the device to be used without any external support;
   a first wing panel rotatably connected to the first side panel; and
   a second wing panel rotatably connected to the second side panel;
   wherein the device can be placed in an open position with edges of the first wing panel and the second wing panel resting on a support surface and with the spine member, the first side panel and the second side panel being spaced from the support surface;
   wherein the first wing panel includes a first notch in a side of the first wing panel opposite the first side panel;

wherein the second wing panel includes a second notch in a side of the second wing panel opposite the second side panel; and wherein the first notch and the second notch allow arms of a patient to be inserted therethrough during treatment of a chest or back of the patient.

9. The convertible lamp array device of claim 8, wherein:
the first side panel is connected to the spine member by at least one first side constant torque hinge; and
the second side panel is connected to the spine member by at least one second side constant torque hinge.

10. A convertible lamp array device comprising:
a spine member having a spine top side and a spine bottom side, the spine member including at least one spine source of light connected to the spine bottom side of the spine member, the spine member also including a first side and a second side;
a first side panel rotatably coimected to the first side of the spine member, the first side panel including a first side panel top side and a first side panel bottom side, the first side panel including at least one first side source of light connected to the first side panel bottom side of the first side panel;
a second side panel rotatably connected to the second side of the spine member, the second side panel including a second side panel top side and a second side panel bottom side, the second side panel including at least one second side source of light connected to the second side panel bottom side of the second side panel;
wherein the first side panel and the second side panel can be rotated in a first direction relative to the spine member to arrange the device in an open position to allow the at least one spine source of light, the at least one first side source of light and the at least one second side source of light to emit light towards a target area;
wherein the first side panel and the second side panel can be rotated in a second direction relative to the spine member to arrange the device in a closed position for storage of the device; and
wherein the device is free standing in the open position to allow the device to be used without any external support; and
wherein the spine member, the first side panel and the second side panel each comprise a plate having a sub-panel connected thereto, the sub-panels of the spine member, the first side panel and the second side panel including the at least one spine source of light, the at least one first side source of light and the at least one second side source of light, respectively.

11. The convertible lamp array device of claim 10, wherein: the sub-panels are removably connected to the plates.

12. A convertible lamp array device comprising:
a spine member having a spine top side and a spine bottom side, the spine member including at least one spine source of light connected to the spine bottom side of the spine member, the spine member also including a first side and a second side;
a first side panel rotatably connected to the first side of the spine member, the first side panel including a first side panel top side and a first side panel bottom side, the first side panel including at least one first side source of light connected to the first side panel bottom side of the first side panel;
a second side panel rotatably connected to the second side of the spine member, the second side panel including a second side panel top side and a second side panel bot-tom side, the second side panel including at least one second side source of light connected to the second side panel bottom side of the second side panel;
a first wing panel rotatably connected to the first side panel;
a second wing panel rotatably connected to the second side panel; and
wherein the device can be placed in an open position with edges of the first wing panel and the second wing panel resting on a support surface and with the spine member, the first side panel and the second side panel being spaced from the support-surface;
wherein the first wing panel and the second wing panel do not include any sources of light.

13. The convertible lamp array device of claim 12, wherein:
the first wing panel is connected to the first side panel by at least one first wing constant torque hinge; and
the second wing panel is connected to the second side panel by at least one second wing constant torque hinge.

14. The convertible lamp array device of claim 12, wherein:
the first side panel is connected to the spine member by at least one first side constant torque hinge; and
the second side panel is connected to the spine member by at least one second side constant torque hinge.

15. The convertible lamp array device of claim 12, wherein:
at least one spine source of light, the at least one first side source of light and the at least one second side source of light each comprise light emitting diodes.

16. The convertible lamp array device of claim 12, wherein:
when the device is in the closed position, a first angle between the spine bottom side of the spine member and the first side panel bottom side is acute, and a second angle between the spine bottom side of the spine member and the second side panel bottom side is acute.

17. The convertible lamp array device of claim 12, further including:
a digital timer connected to the spine member, the first side panel or the second side panel to display and control a duration of light exposure to the patient.

18. The convertible lamp array device of claim 12, further including:
a counter connected to the spine member, the first side panel or the second side panel to record and display a number of hours that the sources of light have been powered.

19. A convertible lamp array device comprising:
a spine member having a spine top side and a spine bottom side, the spine member including at least one spine source of light connected to the spine bottom side of the spine member, the spine member also including a first side and a second side;
a first side panel rotatably connected to the first side of the spine member, the first side panel including a first side panel top side and a first side panel bottom side, the first side panel including at least one first side source of light connected to the first side panel bottom side of the first side panel;
a second side panel rotatably connected to the second side of the spine member, the second side panel including a second side panel top side and a second side panel bot-tom side, the second side panel including at least one second side source of light connected to the second side anel bottom side of the second side panel;

a first wing panel rotatably connected to the first side panel; and a second wing panel rotatably connected to the second side panel;

wherein the device can be placed in an open position with edges of the first wing panel and the second wing panel resting on a support surface and with the spine member, the first side panel and the second side panel being spaced from the support surface;

wherein the first wing panel includes a first notch in a side of the first wing panel opposite the first side panel; and wherein the second wing panel includes a second notch in a side of the second wing panel opposite the second side panel; and wherein the first notch and the second notch allow arms of a patient to be inserted therethrough during treatment of a chest or back of the patient.

20. A convertible lamp array device comprising:

a spine member having a spine top side and a spine bottom side, the spine member including at least one spine source of light connected to the spine bottom side of the spine member, the spine member also including a first side and a second side;

a first side panel rotatably connected to the first side of the spine member, the first side panel including a first side panel top side and a first side panel bottom side, the first side panel including at least one first side source of light connected to the first side panel bottom side of the first side panel;

a second side panel rotatably connected to the second side of the spine member, the second side panel including a second side panel top side and a second side panel bottom side, the second side panel including at least one second side source of light connected to the second side panel bottom side of the second side panel;

a first wing panel rotatably connected to the first side panel; and a second wing panel rotatably connected to the second side panel;

wherein the device can be placed in an open position with edges of the first wing panel and the second wing panel resting on a support surface and with the spine member, the first side panel and the second side panel being spaced from the support surface; and wherein the spine member, the first side panel and the second side panel each comprise a plate having a sub-panel connected thereto, the sub-panels of the spine member, the first side panel and the second side panel including the at least one spine source of light, the at least one first side source of light and the at least one second side source of light, respectively.

21. The convertible lamp array device of claim 20, wherein: the sub-panels are removably connected to the plates.

* * * * *

UNITED STATES PATENT AND TRADEMARK OFFICE
CERTIFICATE OF CORRECTION

| | | |
|---|---|---|
| PATENT NO. | : 7,517,101 B2 | Page 1 of 1 |
| APPLICATION NO. | : 11/691850 | |
| DATED | : April 14, 2009 | |
| INVENTOR(S) | : Stephen M. Tobin et al. | |

It is certified that error appears in the above-identified patent and that said Letters Patent is hereby corrected as shown below:

<u>Title page, item 75</u>
"Inventor: Stephen M. Tobin, 89 Channing Rd., Watertown, MA (US) 02472" should be --Inventor: Stephen M. Tobin, 134 Plymouth Rd., Newton, MA (US) 02461; Paul A. Sowyrda, 2 Tubwreck Drive, Medfield, MA (US) 02052--.

<u>Column 8</u>
Claim 8, line 1, "A lamp" should be --A convertible lamp--.

<u>Column 9</u>
Claim 10, line 18, "coimected" should be --connected--.

<u>Column 10</u>
Line 4, "panel" should be --panel; and--.
Line 6, "panel; and" should be --panel;--.
Line 11, "support-surface" should be --support surface--.
Line 67, "anel" should be --panel--.

<u>Column 11</u>
Line 11, "panel; and" should be --panel;--.

Signed and Sealed this

Eighteenth Day of August, 2009

David J. Kappos
*Director of the United States Patent and Trademark Office*